(12) United States Patent
Yee

(10) Patent No.: US 7,288,082 B2
(45) Date of Patent: Oct. 30, 2007

(54) METHOD AND APPARATUS FOR STERILELY ACQUIRING AND SEPARATING A FLUID

(75) Inventor: Richard W. Yee, Houston, TX (US)

(73) Assignee: SeeFit Incorporated, Houston, TX (US)

( * ) Notice: Subject to any disclaimer, the term of this patent is extended or adjusted under 35 U.S.C. 154(b) by 432 days.

(21) Appl. No.: 10/272,650

(22) Filed: Oct. 17, 2002

(65) Prior Publication Data
US 2004/0078021 A1 Apr. 22, 2004

(51) Int. Cl.
*A61B 19/00* (2006.01)
*B65D 81/00* (2006.01)
*A61B 5/00* (2006.01)

(52) U.S. Cl. ............... 604/410; 604/408; 600/575; 600/579

(58) Field of Classification Search ........... 604/403, 604/408–410, 27, 80, 81, 246, 256, 259, 604/262, 326; 220/62.22, 501; 383/210.1; 206/363–366; 222/134; 600/573, 575, 578–581
See application file for complete search history.

(56) References Cited

U.S. PATENT DOCUMENTS

| | | | |
|---|---|---|---|
| 3,185,154 A | 5/1965 | Caccavo et al. ............ 128/272 |
| 3,187,750 A * | 6/1965 | Tenczar, Jr. ................ 604/410 |
| 3,911,918 A | 10/1975 | Turner ........................ 128/272 |
| 3,965,889 A | 6/1976 | Sachs ............................ 128/2 |
| 4,863,454 A | 9/1989 | LaBove ...................... 604/416 |
| 4,994,039 A * | 2/1991 | Mattson ...................... 604/408 |
| 5,394,907 A | 3/1995 | Hjertman et al. .............. 141/1 |
| 5,496,301 A * | 3/1996 | Hlavinka et al. ........... 604/409 |
| 5,562,836 A * | 10/1996 | Joie et al. ................... 210/782 |
| 5,746,979 A | 5/1998 | Holm ........................... 422/72 |
| 6,146,360 A * | 11/2000 | Rogers et al. .............. 604/151 |
| 2003/0146170 A1 * | 8/2003 | Corbin et al. ............... 210/739 |

FOREIGN PATENT DOCUMENTS

WO   WO8904639   *   6/1989   ................ 604/410

* cited by examiner

*Primary Examiner*—Tatyana Zalukaeva
*Assistant Examiner*—Leslie R. Deak
(74) *Attorney, Agent, or Firm*—Chowdhury & Georgakis, P.C.

(57) ABSTRACT

A method and apparatus are provided by which a fluid may be drawn and packaged within a series of interconnected sterile units. Once filled with the fluid, the connectors joining the sterile units may be sealed and severed to produce a number of separate sterile units. The volume of the separate sterile units may correspond to a single dose of the fluid. The technique allows a fluid to be partitioned into sterile units without exposure to the air or other potential contaminants.

22 Claims, 3 Drawing Sheets

METHOD AND APPARATUS FOR STERILELY ACQUIRING AND SEPARATING A FLUID

BACKGROUND OF THE INVENTION

1. Field of the Invention

The present invention relates generally to the field of storage of biomedical samples and fluids. More specifically, the invention relates to the sterile acquisition and storage of medications and bodily fluids in dosage packaging without exposing the fluids to air and contaminants.

2. Description of the Related Art

This section is intended to introduce the reader to aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

The medical and research communities routinely acquire samples of bodily fluids, such as blood, and store such samples for subsequent use. Similarly, medications, drugs, or research compounds may be prepared and stored in large quantities but may need to be used in substantially smaller doses. In both instances, it is often desirable to provide the fluids in packaging which is easy to store and which corresponds to a usable amount, i.e., a single dose. In the process of placing the fluid into storage containers, however, it is desirable to prevent contact with the air or any other potential contaminant which would compromise the sterility of the fluid packaging.

For example, if a blood sample is drawn from a patient for subsequent division and storage, a technician must either switch sample collection tubes during the process of drawing the blood in order to obtain multiple samples or must draw a single, larger sample which is subsequently divided. In both techniques, there is a risk of contamination due to exposure to air or contact with other non-sterile environments and/or instrumentation. To obviate these risks the sample may be heated or otherwise treated to minimize the risks of contamination. These additional steps may be undesirable and add a level of complexity to the process. It is therefore desirable to provide a means by which a fluid or sample may be obtained and separated into dosage storage containers without introducing the risks associated with air exposure and without necessarily requiring additional treatments, such as heating or irradiation.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
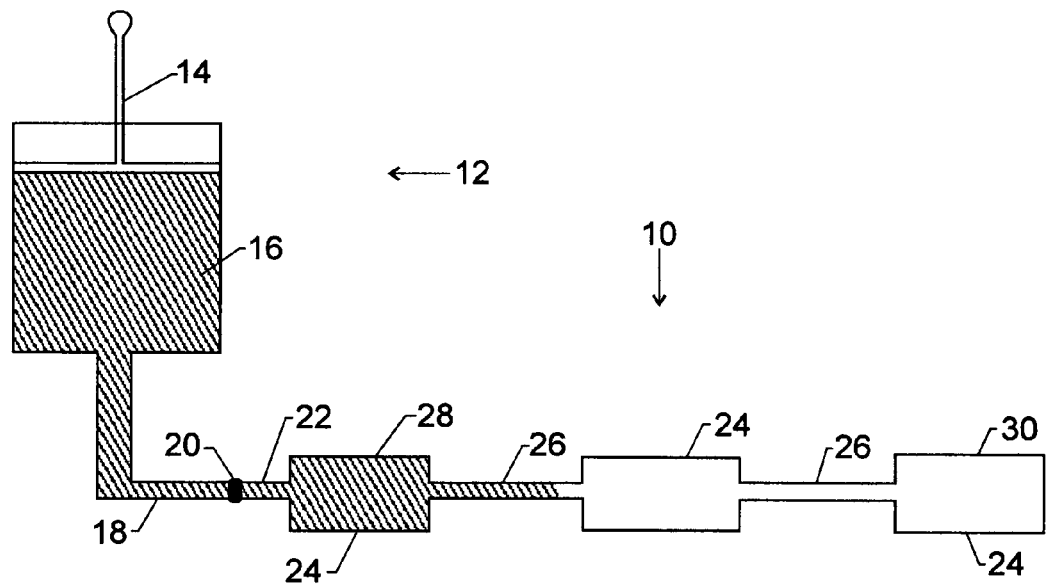
FIG. 1 is a depiction of an apparatus for storing a fluid in the process of filling the sterile chambers of the apparatus with the fluid.

One or more specific embodiments of the present invention will be described below. Turning now to the drawings, and referring initially to FIG. 1, a sterile assembly 10 is depicted which is connected to a fluid source 12. The fluid source 12 can include a pressure regulator 14, here depicted as consisting of a piston action plunger cooperatively configured to apply pressure in an airtight manner to the fluid 16 within the fluid source 12. Alternate pressure regulation configurations are of course possible such as configuring pressure regulator 14 to create an area of negative pressure away from the fluid source 12, see FIG. 5, or combinations of positive and negative pressure within the apparatus. Typically any configuration of one or more pressure regulators 14 which produce a relative negative pressure downstream within sterile assembly 10 is acceptable. In instances in which the sterile assembly 10 is configured for drawing bodily fluids, the sterile assembly 10 may be created as a sterile vacuum or to inherently possess low relative pressure such that the bodily fluid is naturally drawn into the sterile assembly 10.

The fluid source 12 also consists of a fluid outlet 18 terminating in an airtight junction 20. The fluid 16 flows through the fluid outlet 18 due to the pressure differential created by the pressure regulator 14. The fluid 16 typically consists of a drug or medication stored in a stock supply or of a patient's bodily fluid.

In the present technique, the sterile assembly 10 is connected to the airtight junction 20 via a fluid inlet 22 which cooperatively engages the junction 20. The fluid inlet 22 provides fluid access to the remainder of the attached assembly 10, which consists of at least two compartments 24 joined together by a connector 26 which, when open, allows the fluid 16 to flow between the compartments 24. As depicted, the fluid inlet 22 is attached to an upstream terminal compartment 28. Likewise there is a downstream terminal compartment 30 from which the fluid 16 does not flow into another compartment 24. As many compartments 24 as necessary may be included in the assembly 10 in order to provide sufficient storage for the quantity of fluid 16 desired.

Typically the compartments 24 are sized such that they hold a single or multiple dose of the fluid 16 and are therefore uniformly sized in most applications. However, the compartments 24 may be differently sized if the quantity comprising a single dose is to vary over the course of treatment, i.e., dosage gradually tapering off as treatment progresses. The sterile assembly 10 is typically constructed from an airtight material, such as one of the various plastics utilized to make sterile biomedical storage containers. In one embodiment, the assembly is constructed of a sterile, flexible biomedical plastic which is vacuum vacated and sealed such that no contaminants or air are present in the assembly 10 prior to use. In this embodiment, the compartments 24 expand as they are filled with the fluid 16.

As depicted in FIG. 1, the sterile assembly 10 is initially attached to the fluid source 12 via coupling the fluid inlet 22 to the junction 20. The fluid 16 is then introduced into the assembly 10 by the pressure differential created or maintained by the pressure regulator 14. While the apparatus 10 is being filled with the fluid 16, the connectors 26 are open, allowing the fluid 16 to reach and fill all of the compartments 24.

Figure 2:
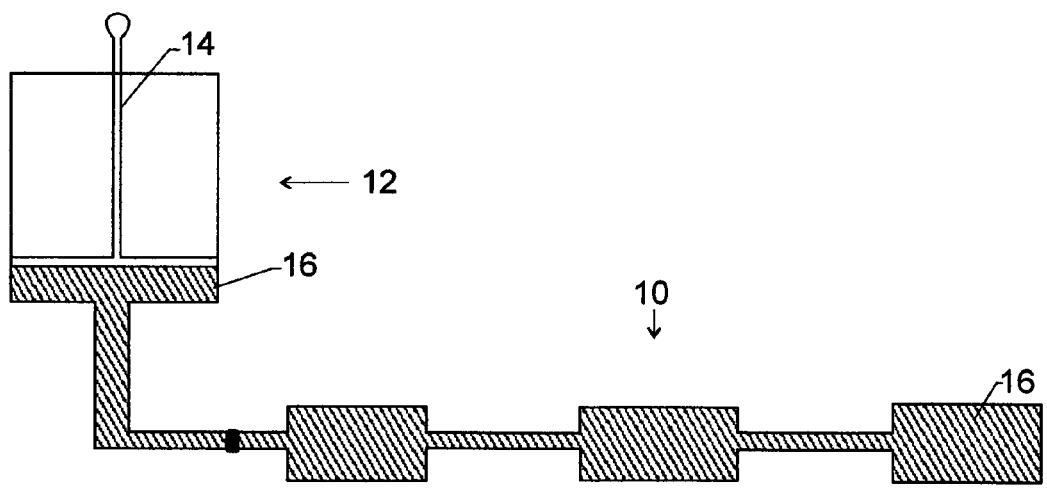
FIG. 2 is a depiction of an apparatus for storing a fluid in which the sterile chambers of the apparatus are filled with the fluid.
Figure 3:
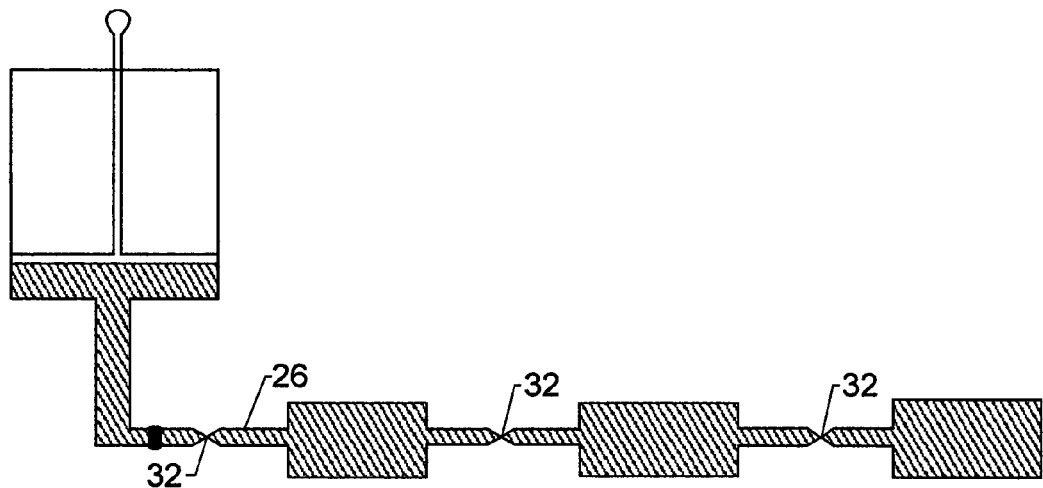
FIG. 3 is a depiction of an apparatus for storing a fluid in which connectors joining the sterile chambers of the filled apparatus have been sealed to form an airtight seal.

Once the sterile assembly 10 is filled with fluid 16, as depicted in FIG. 2, the pressure differential may be equilibrated via the pressure regulator 14. Once the pressure differential is equalized, the connectors 26 are closed by forming an airtight seal 32 within the connector 26, as depicted in FIG. 3. In one embodiment of this technique, the biomedical plastic of which the connectors 26 are composed is a heat-shrink plastic. Upon application of heat to the connector 26, the connector 26 shrinks in volume to form an airtight seal 32. In other embodiments, the connector 26 may be composed of a pressure sensitive material such that pressure may be applied to form the airtight seal 32 or the connector 26 may be constructed with engaging surfaces along the interior which engage to form an airtight seal when moved into contact. In other embodiments, a combination of heat and pressure may be used to affect the seal. Other means by which the airtight seal 32 may be formed exist and are within the scope of the described technique.

Figure 4:
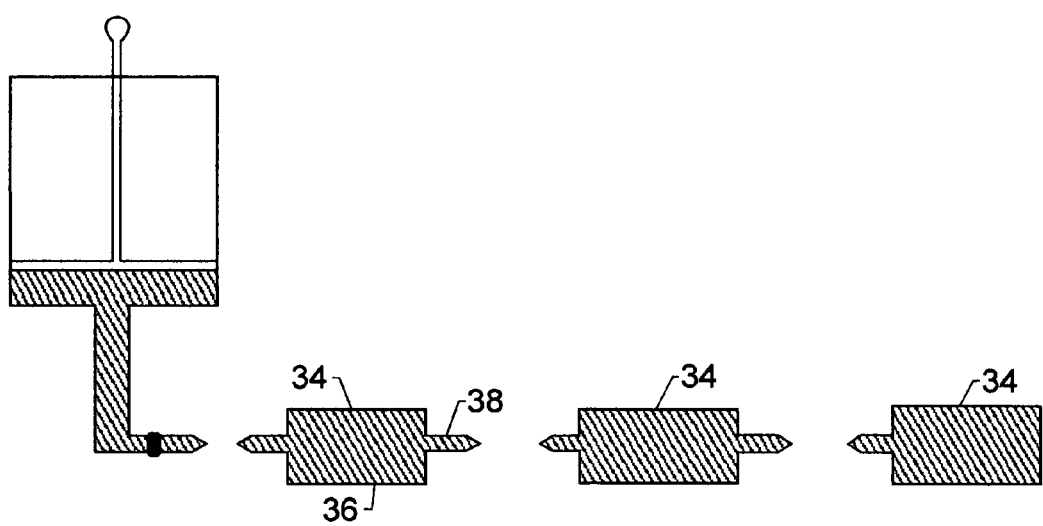
FIG. 4 is a depiction of an apparatus for storing a fluid in which the filled sterile chambers of the apparatus have been separated at the airtight seals to form sealed individual doses of the fluid.

After airtight seal 32 is formed, the compartments 24 may separated from one another at the seal 32, as depicted in FIG. 4. Due to the airtight seal 32, the fluid 16 is never exposed to the air and thus remains sterile. As depicted in FIG. 4, the compartments 24, once separated, form sterile storage containers 34 which may be stored as needed and which each contain a prescribed dose of the fluid 16, ready for use by a doctor or patient. The sterile storage containers 34 consist of a main body 36 and one or more portions of sealed connector 38 which remain associated with the main body 36 after separation. The portions of sealed connector 38 provide easy access to the stored fluid 16, when needed, by either cutting or tearing. In this manner, a single or multiple dose of the fluid 16 may be provided for subsequent application to a patient, test subject or process.

In an alternative embodiment, the sterile assembly 10, once filled, may be sealed by heat or pressure means at the fluid inlet 22. The sterile assembly may then be stored intact. During storage, the seals 32 may or may not be formed in the respective connectors 26. In this embodiment, prior to use or during storage, an airtight seal 32 is be formed in the desired connector and the respective sterile storage container 34 may then be removed from the sterile assembly 10 for use.

In this embodiment a sealing device may be configured to create an airtight seal 32 which does not break symmetrically. The configured sealing device may apply heat, pressure, or a combination of the two via clamping section to form the asymmetric seal. The clamping section is typically configured to conform to the shape of the connector when loose and may tighten to deform the connector as pressure and/or heat are applied. Heat may be generated by elements within the clamping section which utilize infrared, RF, electrical, or chemical energy or other heat generating methods known in the art.

The airtight seal 32 which is created may be formed to break such that the compartments 24 remaining connected to the sterile assembly 10 remain airtight, and thus sterile, while the storage container 34 which is removed is open and ready for use due to the asymmetry of the airtight seal 32 formed. In this manner a filled sterile assembly 10 may be filled, stored and sealed such that, when desired, a sterile storage containers 34 may be removed from the assembly 10 ready for use.

Figure 5:
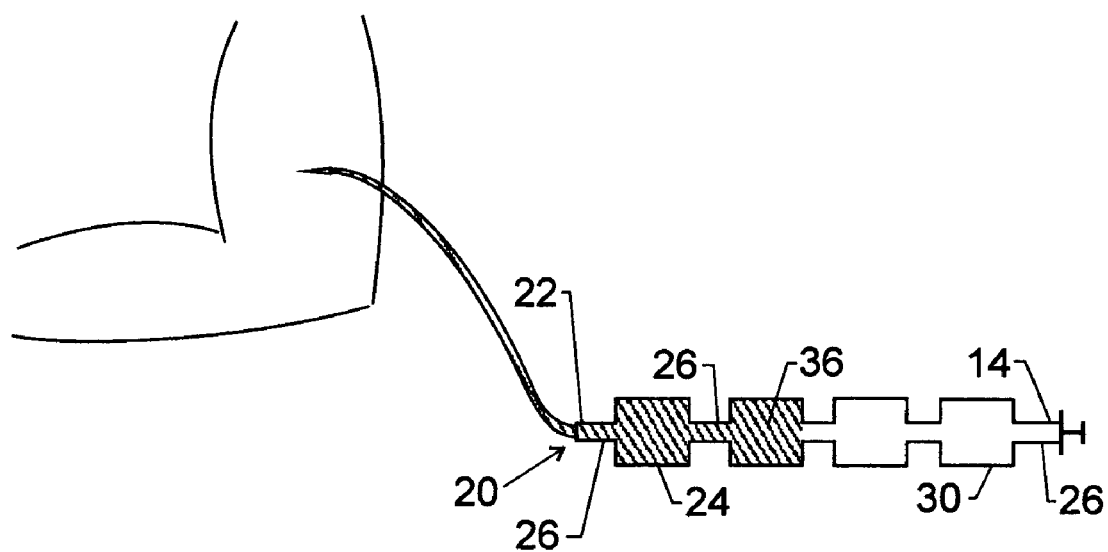
FIG. 5 is a depiction of one exemplary embodiment of the present technique in which a patient's blood is the fluid which is used to fill the apparatus for subsequent storage.

In one exemplary embodiment, the fluid 16 is a patient's blood 36. In this embodiment, the assembly 10 can be utilized while the patient's blood 36 is drawn, as depicted in FIG. 5. The apparatus 10 in this embodiment can utilize negative pressure to fill the compartments 24 with the blood 36 without allowing exposure to the air. In particular, a pressure regulator 14 may be operatively coupled to the terminal compartment 30 to create negative pressure to draw the blood into the apparatus 10. The pressure regulator 14 may operate on a piston principle. Alternately, the apparatus 10 itself may be formed and stored as a vacuum such that the negative pressure of the vacuum draws the blood into it once connected to the patient. As with the previously described embodiment, once the apparatus 10 is filled, the connectors 26 joining the compartments 24 to each other and to the fluid inlet 22 and pressure regulator 14 are sealed and then separated. Once separated, the storage containers of blood may be stored and subsequently used for medicinal purposes, such as for the treatment of certain eye disorders.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method for sterilely collecting fluid comprising:
providing an interconnected sterile assembly comprising an upstream compartment, at least one intermediate compartment joined by a first connector to the upstream compartment, and a downstream compartment joined by a second connector to the intermediate compartment; and
filling the interconnected sterile assembly with a fluid, wherein the fluid passes through the upstream compartment and first connector and the at least one intermediate compartment and second connector to fill the downstream compartment, said filling the interconnected sterile assembly with a fluid accomplished without disconnecting any of the compartments from one another, wherein filling the interconnected sterile assembly with the fluid comprises operating a pressure regulator coupled to the downstream compartment such that pressure within the interconnected sterile assembly can be adjusted.

2. The method as recited in claim 1, further comprising storing the fluid within the interconnected sterile assembly.

3. The method as recited in claim 1, further comprising forming an airtight seal within the connectors connected to each compartment.

4. The method as recited in claim 3, wherein forming the airtight seal within the connectors connected to each compartment comprises at least one of heating and compressing the connectors to form the airtight seal.

5. The method as recited in claim 3, further comprising disconnecting each compartment at each seal such that three or more sterile storage compartments are formed from the disconnected sterile assembly.

6. The method as recited in claim 5, further comprising storing the fluid within the three or more sterile storage compartments.

7. The method as recited in claim 5, further comprising applying a dose of the fluid from one of the sterile storage compartments.

8. The method as recited in claim 1, further comprising drawing a patient's blood and wherein filling the interconnected sterile assembly with the fluid comprises filling the interconnected sterile assembly with the patient's blood.

9. The method as recited in claim 1, further comprising drawing a medication from a sterile stock supply and wherein filling the interconnected sterile assembly with the fluid comprises filling the interconnected sterile assembly with the medication.

10. The method as recited in claim 1, wherein filling the interconnected sterile assembly with the fluid comprises applying positive pressure to fill the interconnected sterile assembly with the fluid.

11. The method as recited in claim 1, wherein filling the interconnected sterile assembly with the fluid comprises applying negative pressure to fill the interconnected sterile assembly with the fluid.

12. An apparatus for storing a fluid comprising:
an interconnected sterile assembly comprising:
  an upstream compartment
    at least one intermediate compartment joined by a first connector to the upstream compartment;
    a downstream compartment joined by a second connector to the intermediate compartment;
  a fluid inlet to the sterile assembly connected to the upstream compartment, wherein fluid passes through the upstream compartment and first connector and the at least one intermediate compartment and second connector to fill the downstream compartment without disconnecting any of the compartments from one another; and
  a pressure regulator operatively coupled to the downstream compartment such that pressure within the apparatus can be adjusted.

13. The apparatus as recited in claim 12, wherein the upstream compartment, downstream compartment, and at least one intermediate compartment are uniformly sized.

14. The apparatus as recited in claim 12, wherein the upstream compartment, downstream compartment, and at least one intermediate compartment are each sized to contain a single dose of the fluid.

15. The apparatus as recited in claim 12, wherein the fluid inlet is a mechanism for drawing blood.

16. The apparatus as recited in claim 12, wherein each connector is closed by an airtight seal and wherein sealed compartments are separable at each airtight seal.

17. The apparatus as recited in claim 16, wherein each airtight seal is at least one of a heat shrink seal and a compression seal.

18. The apparatus as recited in claim 12, wherein the pressure regulator is a piston action pressure regulator.

19. A variable volume fluid container comprising an upstream chamber, at least one intermediate chamber joined by a first connector to the upstream chamber, and a downstream chamber joined by a second connector to the intermediate chamber, wherein the chambers are interconnected in series for sterilely collecting, storing or packaging fluid, wherein a pressure regulator is coupled to the downstream chamber at the end of the series.

20. The variable volume fluid container of claim 19, wherein fluid may be packaged within one or more chambers by sealing one or more connectors joining one or more chambers, wherein the pressure regulator is a piston action pressure regulator.

21. The variable volume fluid container of claim 19, wherein the volume of at least one chamber is different from the volume of one or more other chambers.

22. The variable volume fluid container of claim 19, wherein the variable volume fluid container is evacuated prior to its use to sterilely collect, store or package fluid.

* * * * *